United States Patent [19]
Salimbeni et al.

[11] Patent Number: 5,587,390
[45] Date of Patent: Dec. 24, 1996

[54] IMIDAZOLE DERIVATIVES HAVING A II ANTAGONIST ACTIVITY

[75] Inventors: Aldo Salimbeni; Fabio Paleari; Jacques Mizrahi; Carlo Scolastico, all of Milan, Italy

[73] Assignee: Istituto Luso Farmaco D'Italia S.p.A., Milan, Italy

[21] Appl. No.: 379,468

[22] PCT Filed: Jul. 29, 1993

[86] PCT No.: PCT/EP93/02024

§ 371 Date: Mar. 17, 1995

§ 102(e) Date: Mar. 17, 1995

[87] PCT Pub. No.: WO94/03449

PCT Pub. Date: Feb. 17, 1994

[30] Foreign Application Priority Data

Aug. 7, 1992 [IT] Italy .................... MI92A1951

[51] Int. Cl.$^6$ .................. A61K 31/44; A61K 31/415; C07D 233/56; C07D 401/06
[52] U.S. Cl. .................. 514/341; 514/381; 514/382; 514/396; 548/252; 548/253; 548/254; 548/335.1; 548/343.5; 548/346.1; 546/274.1; 546/272.7
[58] Field of Search .................... 514/341, 381, 514/382, 396; 546/276, 278; 548/252, 253, 254, 335.1, 343.5, 346.1

[56] References Cited

FOREIGN PATENT DOCUMENTS

| 324377 | 7/1989 | European Pat. Off. | 514/396 |
| 479479 | 4/1992 | European Pat. Off. | 514/396 |
| 497121 | 8/1992 | European Pat. Off. | 514/396 |
| 9100281 | 2/1991 | WIPO | 514/396 |

OTHER PUBLICATIONS

CA 115:8809j Preparation . . . Blockers. Ardecky et al. p. 863, 1991.

CA 116:66252x Treatment . . . Antagonists, Carini et al., p. 67, 1992.

CA 120:270398t Imidazole . . . Activity. Salimbemi et al., p. 1070, 1994.

*Primary Examiner*—Joseph K. McKane
*Attorney, Agent, or Firm*—Walter H. Schneider

[57] ABSTRACT

Imidazole derivatives having A II antagonist activity, of Formula I, the processes for the preparation thereof, pharmaceutical compositions containing them and the use thereof as therapeutic agents. The described compounds having A II antagonist activity can be used in various cardiovascular disorders.

11 Claims, No Drawings

IMIDAZOLE DERIVATIVES HAVING A II ANTAGONIST ACTIVITY

This application is a 371 of PCT/EP93/02024 filed Jul. 29, 1995.

The present invention relates to imidazole derivatives having A II antagonist activity, the processes for the preparation thereof, pharmaceutical compositions containing them and the use thereof as therapeutical agents.

The renin-angiotensin system (RAS) is a proteolytic chain which plays a paramount role in the control of blood pressure and is apparently involved in the onset and the maintainement of some cardiovascular disorders, such as hypertension and cardiac decompensation.

The octapeptide hormone angiotensin II (A II), the final product from RAS, mainly forms in the blood following to the degradation of angiotensin I, carried out by the ACE enzyme, which is located in endothelium of blood vessels, lungs, kidney and many other organs. Such an hormone exerts a strong vasoconstricting action on arteries, due to its interaction with specific receptors located on the cell membranes.

One of the possible ways to control RAS is the A II antagonism at the receptor level. Some peptide analogues of A II (for example saralasin, sarmesin) are known to competitively block the interactions of said hormone, however the use thereof, both experimentally and clinically, is restricted by a partial agonist activity and by the lack of activity by the oral route.

Recently, a number of compounds having a non-peptide structure, deriving from 5-membered heterocycles, were described to have II antagonist activity. Examples of these compounds are claimed in patents EP 253,310, EP 324,377, PCT 91/00277, PCT 91/00281 PCT 91/14367, PCT 91/15206, PCT 92/00977.

A common characteristic of these compounds is that they have a completely substituted imidazole ring.

The present invention relates to imidazole derivatives, of general formula (I), having an aryl or heteroaryl group, which can be unsubstituted or functionalized at the 4- or 5-position of the imidazole ring. In the compounds of the invention, an hydrogen atom on the imidazole ring and a biphenylmethyl moiety linked to the imidazole by a nitrogen-carbon bond are always present.

These novel derivatives have A II antagonist properties and they in various can be used in various cardiovascular disorders, such as hypertension, cardiac decompensation, in the myocardial ischemia post-treatment or in intraocular hypertension, glaucoma, some renal diseases and hyperaldosteronism.

The compounds of the invention have general formula (I):

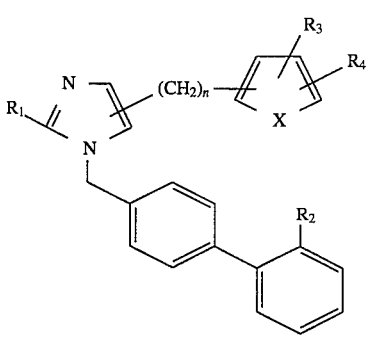

wherein:

n can be 0, 1 or 2

X can be O, S,

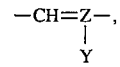

wherein Z can be C or N, whereas Y can be H, when Z is the same as C or can be oxygen or it can be not present, when Z is the same as N;

$R_1$ can be $C_1$–$C_5$ straight, branched or cyclic alkyl, or a $C_2$–$C_5$ alkenyl group;

$R_2$ can be a —COOR$_5$ group, —CN, a SO$_3$H group, or a tetrazole group of general formula (IIa) or (IIb):

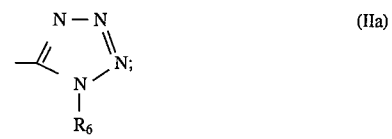

$R_3$, $R_4$ can independently be H, halogen, CN, NO$_2$, NH$_2$, COR$_7$, OR$_8$, CH$_2$OR$_8$, $C_1$–$C_5$ straight or branched alkyl;

$R_5$ can be H, $C_1$–$C_5$ straight or branched alkyl, benzyl;

$R_6$ can be H, $C_1$–$C_5$ alkyl, triphenylmethyl;

$R_7$ can be H, OR$_8$, NR$_9$R$_{10}$;

$R_8$ can be H, $C_1$–$C_5$ straight or branched alkyl, benzyl;

$R_9$, $R_{10}$ can independently be H, $C_1$–$C_5$ alkyl.

The compounds of the invention form salts with various acids and bases, both inorganic and organic, and these also are an object of this invention. Said salts include ammonium salts, salts with alkali metals such as sodium and potassium, salts with alkaline-earth metals such as calcium and magnesium, salts with organic bases such as dicyclohexylamine, N-methyl-D-glucamine, salts with amino acids such as arginine, lysine and the like. The salts with organic and inorganic acids comprise hydrochloric, hydrobromic, sulfuric, phosphoric, methanesulfonic, toluenesulfonic, maleic, fumaric, camphorsulfonic acids and the like.

Examples of $C_1$–$C_5$ alkyl groups are methyl, ethyl, propyl, isopropyl, butyl, isobutyl, tert-butyl, pentyl, isopentyl, cyclopropyl, cyclobutyl, cyclopentyl; preferably methyl, propyl and butyl.

Examples of $C_2$–$C_5$ alkenyl groups are vinyl, allyl, isoprenyl, 2-butenyl, 3-pentenyl.

Examples of —COOR$_5$ groups are carbomethoxy, carbethoxy, carbopropoxy, carboisobutoxy, carbotertbutoxy, carbobenzyloxy; preferably carbomethoxy.

Examples of —OR$_8$ groups are methoxy, ethoxy, propoxy, isopropoxy, butoxy, tert-butoxy, pentyloxy.

Examples of —NR$_9$R$_{10}$ groups are methylamino, ethylamino, propylamino, isopropylamino, butylamino, tert-butylamino, dimethylamino, diethylamino, N-methyl-N-ethylamino, N-methyl-N-butylamino, isopentylamino, N-methyl-N-cyclopropylamino.

Preferred compounds of formula (I) are those in which the aryl or heteroaryl group of general formula:

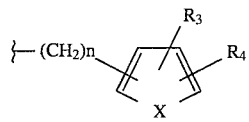

is linked at the 4-position of the imidazole ring and wherein n, X, $R_3$, $R_4$ have the meanings reported for general formula (I).

Other preferred compounds are those in which the aryl or heteroaryl group of general formula

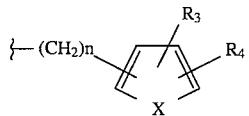

is linked at the 5-position of the imidazole ring and wherein n, X, $R_3$, $R_4$ have the meanings reported for general formula (I).

Particularly preferred compounds are those in which the aryl or heteroaryl group of formula

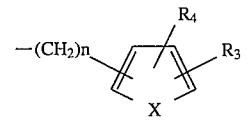

wherein X is —CH=CH—, O, S, —C=N,

$R_3$ is a —COOH group, —COOCH$_3$, —CH$_3$, —OH, is linked at the 4- or 5-position of the imidazole ring and $R_1$ is propyl or butyl.

Most preferred compounds are the following ones:
2-butyl-4-(2-carboxyphenyl)-1-[[2'-(1H-tetrazol-5-yl)biphenyl-4-yl]methyl]-1H-imidazole;
2-butyl-4-(3-carboxyphenyl)-1-[[2'-(1H-tetrazol-5-yl)biphenyl-4-yl]methyl]-1H-imidazole;
2-butyl-4-(4-carboxyphenyl)-1-[[2'-(1H-tetrazol-5-yl)biphenyl- 4-yl]methyl]-1H-imidazole;
2-butyl-5-(2-carboxyphenyl)-1-[[2'-(1H-tetrazol-5-yl)biphenyl-4-yl]methyl]-1H-imidazole;
2-butyl-4-(2-carboxyphenyl)-1-[(2'-carboxybiphenyl-4-yl)methyl]-1H-imidazole;
2-butyl-4-(pyridin-2-yl)-1-[[2'-(1H-tetrazol-5-yl)biphenyl-4-yl]methyl]-1H-imidazole;
2-butyl-5-(3-carboxythiophen-2-yl)-1-[[2'-(1H-tetrazol-5-yl)biphenyl-4-yl]methyl]-1H-imidazole;
2-butyl-5-(3-carboxyfuran-2-yl)-1-[[2'-(1H-tetrazol-5-yl)biphenyl-4-yl]methyl]-1H-imidazole;
2-butyl-4-(pyridin-3-yl)-1-[[2'-(1H-tetrazol-5-yl)biphenyl-4-yl]methyl]-1H-imidazole;
2-butyl-4-(pyridin-4-yl)-1-[[2'-(1H-tetrazol-5-yl)biphenyl-4-yl]methyl]-1H-imidazole;
2-butyl-4-(4-methylpyridin-2-yl)-1-[[2'-(1H-tetrazol-5-yl)biphenyl-4-yl]methyl]-1H-imidazole;
2-butyl-4-(6-methylpyridin-2-yl)-1-[[2'-(1H-tetrazol-5-yl)biphenyl-4-yl]methyl]-1H-imidazole;
2-butyl-4-(4,6-dimethylpyridin-2-yl)-1-[[2'-(1H-tetrazol-5-yl)biphenyl-4-yl]methyl]-1H-imidazole;
2-butyl-4-(pyridin-2-yl-N-oxide)-1-[[2'-(1H-tetrazol-5-yl)biphenyl-4-yl]methyl]-1H-imidazole;
2-butyl-4-(pyridin-3-yl-N-oxide)-1-[[2'-(1H-tetrazol-5-yl)biphenyl-4-yl]methyl]-1H-imidazole;
2-butyl-4-(pyridin-4-yl-N-oxide)-1-[[2'-(1H-tetrazol-5-yl)biphenyl-4-yl]methyl]-1H-imidazole;
2-butyl-4-(4-methylpyridin-2-yl-N-oxide)-1-[[2'-(2H-tetrazol-5-yl)biphenyl-4-yl]methyl]-1H-imidazole;
2-butyl-4-(6-methylpyridin-2-yl-N-oxide)-1-[[2'-(1H-tetrazol-5-yl)biphenyl-4-yl]methyl]-1H-imidazole;
2-butyl-4-(4,6-dimethylpyridin-2-yl-N-oxide)-1-[[2'-(1H-tetrazol-5-yl)biphenyl-4-yl]methyl]-1H-imidazole;
2-butyl-4-(3-carboxyfuran-2-yl)-1-[[2'-(1H-tetrazol-5-yl)biphenyl-4-yl]methyl]-1H-imidazole;
2-butyl-4-(3-carboxythiophen-2-yl)-1-[[2'-(1H-tetrazol-5-yl)biphenyl-4-yl]methyl]-1H-imidazole;
2-butyl-4-(pyridin-2-yl)-1-[(2'-carboxybiphenyl-4-yl)methyl]-1H-imidazole;
2-butyl-4-(pyridin-2-yl-N-oxide)-1-[(2'-carboxybiphenyl-4-yl)methyl]-1H-imidazole;
2-butyl-4-[3-(methoxycarbonyl)thiophen-2-yl]-1-[[2'-(1H-tetrazol-5-yl)biphenyl-4-yl]methyl]-1H-imidazole;
2-butyl-4-(6-hydroxypyridin-2-yl)-1-[[2'-(1H-tetrazol-5-yl)biphenyl-4-yl]methyl]-1H-imidazole.

The invention also relates to the processes for the preparation of the compounds of general formula (I).

According to the invention, the compounds of general formula (I) can be prepared by reacting intermediates of general formula (III), the preparation of which is described in literature (see for example D. J. Carini, et al., J.Med.Chem., 34, 2525, (1991))

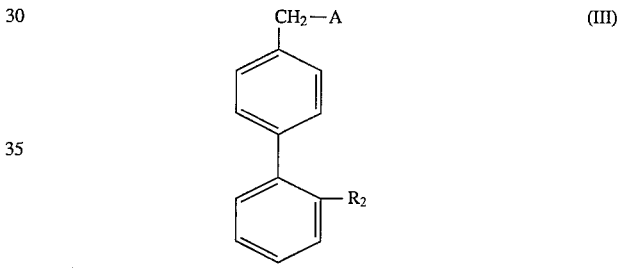

wherein $R_2$ can be a CN, COOR$_5$ group (with $R_5$ lower alkyl or benzyl) or a tetrazole group of general formula (IIa) or (IIb), in which $R_6$ can be $C_1$–$C_5$ alkyl or triphenylmethyl and A can be Cl, Br, I, OCOCH$_3$, OSO$_2$CH$_3$, OSO$_2$CF$_3$, with the compounds of general formula (IV)

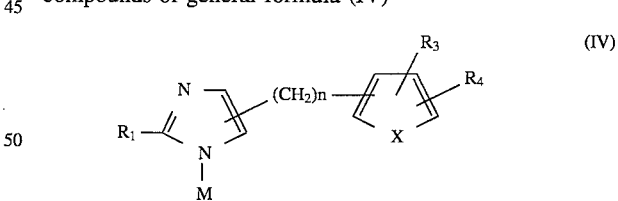

wherein $R_1$, $R_3$, $R_4$, n, X have the same meanings reported for the general formula (I) and M is H, —COCH$_3$, p-methoxybenzyl.

The alkylation reaction can be carried out either forming the imidazole salt (IV), in which M is H, in an aprotic dipolar solvent such as DMF or DMSO by treatment with alkali or alkaline-earth metal hydrides (Na, K, Ca) or alternatively operating in lower alcohols (MeOH, EtOH, t-BuOH) in the presence of the corresponding Na or K alkoxide, at temperatures ranging from 20° C. to 100° C.

Generally, if the alkylation proceeds through formation of the imidazole salt of formula (IV), the corresponding product (single) of general formula (I) which is obtained, always has the aryl or heteroaryl substituent of general formula:

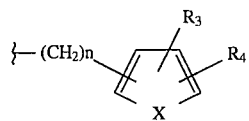

at the 4-position on the imidazole ring. The regioselective synthesis of the derivatives of general formula (I), in which the aryl or heteroaryl group of general formula:

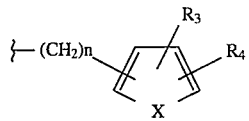

is at the 5-position of the imidazole ring is obtained by reacting the compounds of general formula (IV), in which M can be for example —COCH$_3$ or p-methoxybenzyl, with compounds of general formula (III), in which A is —OSO$_2$CF$_3$, Br and R$_2$ can be CN, COOR$_5$ (with R$_5$ lower alkyl, benzyl), tetrazole (with R$_6$ triphenylmethyl, lower alkyl) in solvents which preferably are CH$_2$Cl$_2$, CHCl$_3$, tetrahydrofuran, acetonitrile at temperatures ranging from −78° C. to 80° C.

The compounds of general formula (I), in which R$_1$, R$_3$, R$_4$, n, X have the same meanings reported above and R$_2$ is a —COOR$_5$ (with R$_5$ hydrogen) or tetrazole group (with R$_6$ hydrogen), can be prepared by acid or alkali hydrolysis of the corresponding derivatives in which R$_2$ is a CN group, R$_5$ is lower alkyl or benzyl, R$_6$ is triphenylmethyl.

The acid hydrolysis can be performed with sulfuric, hydrochloric, trifluoroacetic, formic, acetic acids, both in protic solvents, such as water-lower alcohols mixtures, and in aqueous mixtures of aprotic solvents, such as tetrahydrofuran, dioxane, chloroform. The alkali hydrolysis can be carried out using aqueous solutions or water-lower alcohols mixtures, using inorganic bases such as NaOH, KOH, LiOH at temperatures ranging from 20° C. to 100° C.

When R$_6$ is triphenylmethyl and R$_5$ is benzyl, the protection can be removed by hydrogenolysis in methanol or ethanol, either in the presence or in the absence of acid catalysis.

The compounds of general formula (I), in which R$_3$ or R$_4$ are a carboxylic group, can be obtained by hydrolysis of the corresponding derivatives, in which R$_3$ or R$_4$ can be a CN or COOR$_5$ group (with R$_5$ lower alkyl or benzyl). Alternatively, said compounds can be obtained from derivatives in which R$_3$ or R$_4$ is bromine, by treatment with BuLi and subsequent reaction with gaseous CO$_2$.

By reacting the above bromo-derivatives with BuLi and chlorocarbonates of general formula ClCOOR$_8$ (wherein R$_8$ is lower alkyl or benzyl), the corresponding alkoxycarbonyl- or benzyloxycarbonyl derivatives are obtained, which can be hydrolyzed to the corresponding acids.

Alternatively, the compounds of formula (I) in which R$_2$ is a tetrazole group of formula (IIa) or (IIb), can be obtained from the corresponding compounds in which R$_2$ is CN by treatment with NaN$_3$ and NH$_4$Cl in DMF at 110° C., or preferably by reaction with trialkyl tin azides in toluene or xylene at the solvent boiling temperature.

The intermediates of general formula (IV) can easily be obtained through a series of known procedures.

A method consists in reacting ketones of general formula (V):

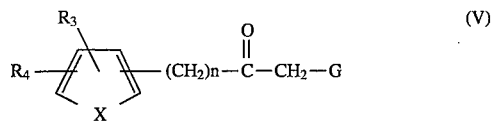

wherein R$_3$, R$_4$, n, X have the same meanings as in general formula (I) and G can be Cl, Br, OH, NH$_2$, with compounds of general formula (VI):

wherein R$_1$ has the same meanings as in general formula (I) and B is a NH$_2$, —OCH$_3$, —OCH$_2$CH$_3$ group (as described for example by F. Kunckell, Ber., 34, 637, (1901)), or reacting compounds of general formula (V), in which G is a R$_1$CONH— or R$_1$COO— group, with ammonia or formamide (as described for example by D. Davidson et al., J. Org. Chem. 2, 319 (1937), H. Bredeseck et al., Ber., 85, 1351 (1955)).

An alternative method for the preparation of compounds (I) consists in reacting imidazoles of general formula (VII)

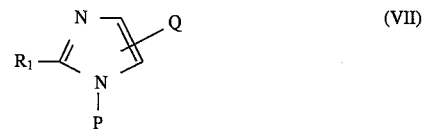

in which R$_1$ has the meanings reported above, P can be a protecting group such as —CH$_2$OCH$_2$CH$_2$Si(CH$_3$)$_3$, —CH$_2$N(CH$_3$)$_2$ and Q can be ZnCl, Bu$_3$Sn, Me$_3$Sn, B(OH)$_2$, or I or Br, with compounds of general formula (VIII):

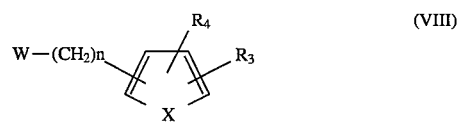

wherein n, X, R$_3$, R$_4$ have the meanings reported above and W can be I or Br, or ZnCl, Bu$_3$Sn, Me$_3$Sn, B(OH)$_2$, in the presence of transition metal complexes as catalysts, such as palladium, platinum, nickel complexes, (as described for example from M. Peyeyre et al., Tin in organic synthesis, ButterWorths, London, 1987; R. F. Heck, Palladium Reagents in organic chemistry, Academic Press, Orlando, Fla., 1985), and subsequent reaction with a compound of formula (III) described above.

Compounds of general formula (I), in which X is

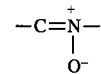

and n, R$_1$, R$_2$, R$_3$, R$_4$ have the meanings reported above, can be obtained starting from the corresponding derivatives of general formula (I), in which X is —C═N— and n, R$_1$, R$_2$, R$_3$, R$_4$ have the meanings reported above, by treatment with organic or inorganic peracids. For example, hydrogen peroxide in a 20–30% aqueous solution can be used in the presence of varying amounts of glacial acetic acid, or perbenzoic acid or 3-chloroperbenzoic acid in solvents which preferably are dichloromethane or chloroform, at temperatures ranging from 0° C. to 80° C.

When one of the substituents R$_3$ or R$_4$ present on the pyridine ring is methyl and is at the position adjacent to the pyridine nitrogen, the treatment with acetic anhydride and the subsequent hydrolysis of the intermediate acetoxy derivative yields compounds of general formula (I) in which the substituent $R_3$ or $R_4$ is an hydroxymethyl group.

By further oxidation of the latter (for example as described by J. I. De Graw et al., J.Het.Chem., 15, 217 (1978)) with oxidizing agents such as $Cr^{6+}$ salts, manganese dioxide or still other known from literature, intermediates in which $R_3$ or $R_4$ are a formyl, carboxyl, alkoxycarbonyl group can be obtained.

As far as the introduction, handling and transformation of the $R_3$ and $R_4$ functional groups optionally present on the aryl or heteroaryl substituents, the used techniques are generally known to those skilled in the art from literature, as well as the possible protections and deprotections of the functional groups and the sequence of the required transformations.

The compounds described in the present invention act as antagonists at the A II receptor level.

For the characterization and the evaluation of the effectiveness of the compounds of the invention, in vitro tests (such as the inhibition of the A II-induced contraction in the rabbit aorta and the displacement of $^{125}I$-$Sar^1$-$Ile^8$-AT II or [$H^3$] AT II in the rat adrenal cortex) and an in vivo test (the inhibition of the A II-induced pressory response in the ganglio-blocked normotensive rat) were selected. The compounds of invention have shown a remarkable activity in the above tests; for example, in the in vitro tests, a number of compounds turned out to have $pA_2$ values higher than 6.5, whereas they showed to have a Ki <1 μM in the receptor binding test.

For example the compound 2-butyl-4-(pyridin-2-yl-N-oxide)-1-[[2'-(1H-tetrazol-5-yl)biphenyl-4-yl]methyl-1H-imidazole (example 10e) possesses a Ki value of 6.5 nM in the receptor binding test and an $ED_{50}$ value of 0.54 mg/kg/iv in the in vivo test.

Another claimed compound, 2-butyl-4-(2-carboxyphenyl)-1-[[2'-(1H-tetrazol-5-yl)biphenyl-4-yl]methyl]-1H-imidazole (example 10) possesses a $pA_2$ value of 8, whereas in the in vivo test it shows an $ED_{50}$ value of 0.52 mg/kg/iv.

The compounds (I) or the pharmaceutically acceptable salts thereof can be used in pharmaceutical preparations, alone or in admixture with pharmaceutically acceptable excipients, for the oral or parenteral administrations. Suitable excipients are for example starch, lactose, glucose, arabic gum, stearic acid and the like. The pharmaceutical preparations can be in solid form such as tablets, capsules or suppositories or in liquid form, such as solutions, suspensions or emulsions.

Moreover, if administered parenterally, the pharmaceutical preparations can be in form of sterile solutions.

The compounds (I) can be administered in unit doses ranging from 1 to 100 mg to patients suffering from cardiac and vascular disorders, such as hypertension, acute and chronic cardiac decompensations, intraocular hypertension. However, a use can be envisaged also for other disorders, such as secondary hyperaldosteronism, pulmonary hypertension, renal diseases (glomerulonephritis, diabetic nephropathy) or vascular disorders (hemicrania, Raynaud's disease).

The following examples further illustrate the invention.

M.p. are not corrected; the identity of the substances was established by means of elementary analysis (C, H, N) and IR, UV, NMR (200 MHz) and mass spectroscopies. Flash chromatographies (FC) were carried out on silica gel according to the procedures by W. C. Still, J.Org.Chem. 43, 2923 (1978).

EXAMPLE 1

2-Butyl-4(5)-(2-bromophenyl)-1H-imidazole 6.6 g of valeramidine hydrochloride are dissolved in 10 ml of 20% NaOH and extracted with 60 ml of $CHCl_3$. The organic phase is dried over, $Na_2SO_4$ and the clear solution obtained upon filtration is added to 4.5 g of 2-bromo-1-(2-bromophenyl)ethanone dissolved in 40 ml of $CHCl_3$.

The reaction mixture is heated under reflux for 2h, then the solvent is evaporated off under reduced pressure.

The residue is redissolved in 100 ml of AcOEt and washed more times first with water, then with a NaCl saturated solution, then it is dried over $Na_2SO_4$ and the solvent is evaporated off under reduced pressure.

The crude product is purified by means of flash chromatography (eluent: hexane: AcOEt 65:35) to obtain 2.4 g of a beige solid (yield: 53%). M.p.: 90°–92° C.

$^1H$ NMR (200 MHz, $CDCl_3$).

δ: 0.89 (t, 3H); 1.37 (m, 2H); 1.68 (m, 2H); 2.71 (t, 2H); 7.03–7.83 (m, 5H).

The following compounds are prepared according to the same procedure:

2-butyl-4(5)-(3-bromophenyl)-1H-imidazole;
2-butyl-4(5)-(4-bromophenyl)-1H-imidazole;
2-butyl-4(5)-(pyridin-2-yl)-1H-imidazole (a);
2-butyl-4(5)-(pyridin-3-yl)-1H-imidazole (b);
2-butyl-4(5)-(pyridin-4-yl)-1H-imidazole;
2-butyl-4(5)-(6-methylpyridin-2-yl)-1H-imidazole (c);
2-butyl-4(5)-(4-methylpyridin-2-yl)-1H-imidazole;
2-butyl-4(5)-(4,6-dimethylpyridin-2-yl)-1H-imidazole (d);
2-butyl-4(5)-[3-(methoxycarbonyl)furan-2-yl]-1H-imidazole;
2-butyl-4(5)-[3-(methoxycarbonyl)thiophen-2-yl]-1H-imidazole (e).

(a) $^1H$ NMR (200 MHz, $CDCl_3$).

δ: 0.88 (t, 3H); 1.38 (m, 2H); 1.70 (m, 2H); 2.73 (t, 2H); 7.09 (m, 1H); 7.47 (s, 1H); 7.67 (m, 2H); 8.47 (m, 1H).

(b) $^1H$ NMR ($CDCl_3$).

δ: 0.93 (t, 3H); 1.45 (m, 2H); 1.78 (m, 2H); 2.79 (t, 2H); 7.28 (s, 1H); 7.30 (m, 1H); 8.04 (m, 1H); 8.45 (dd, 1H); 8.93 (dd, 1H).

(c) $^1H$ NMR ($CDCl_3$).

δ: 0.94 (t, 3H); 1.42 (m, 2H); 1.78 (m, 2H); 2.53 (s, 3H); 2.77 (t, 2H); 6.95 (d, 1H); 7.43 (s, 1H); 7.43–7.62 (m, 2H).

(d) $^1H$ NMR ($CDCl_3$).

δ: 0.90 (t, 3H); 1.35 (m, 2H); 1.70 (m, 2H); 2.31 (s, 3H); 2.46 (s, 3H); 2.73 (t, 2H); 6.79 (s, 1H); 7.27 (s, 1H); 7.42 (s, 1H).

(e) $^1H$ NMR ($CDCl_3$).

δ: 0.95 (t, 3H); 1.50 (m, 2H); 1.80 (m, 2H); 2.79 (t, 2H); 3.90 (s, 3H); 7.01 (d, 1H); 7.38 (d, 1H+1H).

EXAMPLE 2

1-(N-acetyl)-2-butyl-4-(2-bromophenyl)-1H-imidazole 2.3 g of 2-butyl-4(5)-(2-bromophenyl)-1H-imidazole are dissolved in 20 ml of acetic anhydride at 0° C. The reaction mixture is stirred for 1h at 0° C., then it is left to warm to room temperature and stirred for 8h. Solvent is evaporated off under reduced pressure, the residue is redissolved in 100 ml of $CH_2Cl_2$ and is washed first with a $NaHCO_3$ saturated solution and then with a NaCl saturated solution, dried over $Na_2SO_4$ and the solvent is evaporated off under reduced pressure. 2.2 g of a yellow oil are obtained (Yield: 95%).

$^1H$ NMR ($CDCl_3$): δ 0.96 (t, 3H); 1.44 (m, 2H); 1.74 (m, 2H); 2.62 (s, 3H); 3.08 (t, 2H); 7.15 (m, 1H); 7.37 (m, 1H); 7.62 (dd, 1H); 7.93 (s, 1H); 8.03 (dd, 1H).

The following compounds are prepared according to the same procedure:

1-(N-acetyl)-2-butyl-4-[3-(methoxycarbonyl)furan-2-yl]-1H-imidazole;

1-(N-acetyl)-2-butyl-4-[3-(methoxycarbonyl)thiophen-2-yl]-1H-imidazole.

EXAMPLE 3

4-(Acetoxymethyl)-2'-(1-triphenylmethyltetrazol-5-yl)biphenyl 10.0 g of 4-(bromomethyl)-2'-(1-triphenylmethyltetrazol-5-yl)biphenyl and 3.5 g of cesium acetate are suspended in 300 ml of anhydrous DMF and stirred at 45° C. for 24 h. The solvent is evaporated off under reduced pressure and the residue is taken up in water, to obtain a solid which can easily be filtered. After drying, the solid is triturated with an hexane: ethyl acetate mixture (4:1) to obtain 7.2 g of a beige powder (Yield: 75%).
M.p.: 117°–119° C.
$^1$H-NMR (CDCl$_3$) δ: 2.05 (s, 3H); 5.00 (s, 2H); 6.80–7.50 (m, 22H); 7.95 (m, 1H).

The following compounds are prepared according to the same procedure:
4-(acetoxymethyl)-2'-cyanobiphenyl. M.p.: 78°–80° C.
$^1$H-NMR (CDCl$_3$) δ: 2.14 (s, 3H); 5.17 (s, 2H); 7.40–7.80 (m, 8H).

EXAMPLE 4

4-(Hydroxymethyl)-2'-(1-triphenylmethyltetrazol-5-yl)biphenyl 3.4 g of 4-(acetoxymethyl)-2'-(1-triphenylmethyltetrazol-5-yl)biphenyl dissolved in 30 ml of anhydrous THF, are dropped during 0.5h into a suspension of 0.5 g of LiAlH$_4$ in 20 ml of anhydrous THF at 0° C. The mixture is stirred for 24h at 0° C., then a stoichiometric amount of water is added to decompose LiAlH$_4$ and the precipitated salts are filtered off. The solution is evaporated and the residue is triturated with an hexane:ethyl acetate mixture (9:1). Upon filtration and drying, 2.6 g of a white powder are obtained (Yield: 83%).
M.p.: 167° C.
$^1$H-NMR (CDCl$_3$) δ: 4.58 (d, 2H); 6.91–7.53 (m, 22H); 7.95 (m, 1H).

The following compound is prepared according to the same procedure:
4-(hydroxymethyl)-2'-cyanobiphenyl
M.p.: 120°–122° C.
$^1$H-NMR (CDCl$_3$) δ: 4.78 (d, 2H); 7.45–7.82 (m, 8H).

EXAMPLE 5

2-Butyl-4-(2-bromophenyl)-1-[[2'-(1-triphenylmethyltetrazol-5-yl)biphenyl-4-yl]methyl]-1H-imidazole A suspension of 0.1 g of NaH in 6 ml of anhydrous DMF under nitrogen atmosphere is added with 0.5 g of 2-butyl-4(5)-(2-bromophenyl)-1H-imidazole dissolved in 5 ml of anhydrous DMF. The mixture is stirred at room temperature for 0.5 h, then 1.0 g of 4-(bromomethyl)-2'-(1-triphenylmethyltetrazol-5-yl)biphenyl dissolved in 10 ml of anhydrous DMF are added. Stirring is continued for 16h at room temperature, the solvent is evaporated off under reduced pressure and the oily residue is taken up with 20 ml of water. A solid precipitates which is filtered, washed with water and dried, purified by means of flash chromatography (eluent: hexane: AcOEt 75:35) to obtain 0.8 g of a spongy light yellow solid (Yield: 65%).
$^1$H NMR (CDCl$_3$) δ: 0.89 (t, 3H); 1.30–1.50 (m, 2H); 1.60–1.80 (m, 2H); 2.61 (t, 2H); 4.99 (s, 2H); 6.80–8.15 (m, 28H).

The following compounds are prepared according to the same procedure:
2-butyl-4-(3-bromophenyl)-1-[[2'-(1-triphenylmethyltetrazol-5-yl)biphenyl-4-yl]methyl]-1H-imidazole;
2-butyl-4-(4-bromophenyl)-1-[[2'-(1-triphenylmethyltetrazol-5-yl)biphenyl-4-yl]methyl]-1H-imidazole;
2-butyl-4-(pyridin-2-yl)-1-[[2'-(1-triphenylmethyltetrazol-5-yl)biphenyl-4-yl]methyl]-1H-imidazole (a);
2-butyl-4-(pyridin-3-yl)-1-[[2'(1-triphenylmethyltetrazol-5-yl)biphenyl-4-yl]methyl]-1H-imidazole (b);
2-butyl-4-(pyridin-4-yl)-1-[[2'-(1-triphenylmethyltetrazol-5-yl)biphenyl-4-yl]methyl]-1H-imidazole;
2-butyl-4-(6-methylpyridin-2-yl)-1-[[2'-(1-triphenylmethyltetrazol-5-yl)biphenyl-4-yl]methyl]-1H-imidazole (c);
2-butyl-4-(4-methylpyridin-2-yl)-1-[[2'-(1-triphenylmethyltetrazol-5-yl)biphenyl-4-yl]methyl]-1H-imidazole;
2-butyl-4-(4,6-dimethylpyridin-2-yl)-1-[[2'-(1-triphenylmethyltetrazol-5-yl)biphenyl-4-yl]methyl]-1H-imidazole (d);
2-butyl-4-[3-(methoxycarbonyl)furan-2-yl]-1-[[2'-(1-triphenylmethyltetrazol-5-yl)biphenyl-4-yl]methyl]-1H-imidazole;
2 -butyl-4-[3-(methoxycarbonyl)thiophen-2-yl]-1-[[2'-(1-triphenylmethyltetrazol-5-yl)biphenyl-4-yl]methyl]-1H-imidazole (e);
2-butyl-4-[2-(methoxycarbonyl)phenyl]-1-[[2'-(methoxycarbonyl)biphenyl-4-yl]methyl]-1H-imidazole;
2-butyl-4-(2-bromophenyl)-1-[(2'-cyanobiphenyl-4-yl)methyl]-1H-imidazole;
2-butyl-4-(pyridin-2-yl)-1-[[2'-(methoxycarbonyl)biphenyl-4-yl]methyl]-1H-imidazole (f);
2-butyl-4-(pyridin-2-yl-N-oxide)-1-[[2'-(methoxycarbonyl)biphenyl-4-yl]methyl]-1H-imidazole.

(a) $^1$H NMR (CDCl$_3$).
δ: 0.90 (t, 3H); 1.37 (m, 2H) 1.71 (m, 2H); 2.65 (t, 2H); 4.96 (s, 2H); 6.80–8.51 (m, 28H).

(b) $^1$H NMR (CDCl$_3$).
δ: 0.91 (t, 3H); 1.41 (m, 2H); 1.68 (m, 2H); 2.67 (t, 2H); 4.97 (s, 2H); 6.83–7.50 (m, 24H); 8.00 (m, 2H); 8.42 (dd, 1H); 8.83 (dd, 1H).

(c) $^1$H NMR (CDCl$_3$).
δ: 0.89 (t, 3H); 1.38 (m, 2H); 1.70 (m, 2H); 2.51 (s, 3H); 2.65 (t, 2H); 4.96 (s, 2H); 6.83–7.95 (m, 27H).

(d) $^1$H NMR (CDCl$_3$).
δ: 0.89 (t, 3H); 1.39 (m, 2H); 1.70 (m, 2H); 2.31 (s, 3H); 2.48 (s, 3H); 2.68 (t, 2H); 4.95 (s, 2H); 6.80–8.00 (m, 26H).

(e) $^1$H NMR (CDCl$_3$).
δ: 0.86 (t, 3H); 1.32 (m, 2H); 1.58 (m, 2H); 2.60 (m, 2H); 3.77 (s, 3H); 6.80–8.00 (m, 26H).

(f) $^1$H NMR (CDCl$_3$).
δ: 0.92 (t, 3H); 1.42 (m, 2H); 1.65 (m, 2H); 2.73 (t, 2H); 3.65 (s, 3H); 5.15 (s, 2H); 7.15–7.94 (m, 12H); 8.51 (d, 1H).

EXAMPLE 6

2-Butyl-4-(2-bromophenyl)-1-[[2'-(1-triphenylmethyltetrazol- 5-yl)biphenyl-4-yl]methyl]-1H-imidazole A solution of 0.47 g of 2-butyl-4-(2-bromophenyl)-[(2'-cyanobiphenyl-4-yl)methyl]-1H-imidazole (obtainable according to Example 5) in 7 ml of toluene is added with 0.065 g of NaN$_3$ and 0.33 g of Bu$_3$SnCl. The reaction mixture is refluxed for 120h, cooled to 25° C., added with 0.12 ml of 10N NaOH and 0.28 g of trityl chloride and stirred for further 4h at 25° C. The solution is diluted with 5 ml of water and 10 ml of hexane, keeping stirring for 0.5h. The phases are separated, the organic phase is washed with water and subsequently with a NaCl saturated solution, dried over Na$_2$SO$_4$ and the solvent is evaporated off under reduced pressure. After purification by means of flash chromatography (eluent: hexane: AcOEt 70:30), 0.26 g of a beige spongy solid are obtained. (Yield: 35%).

$^1$H NMR (CDCl$_3$) δ: 0.89 (t, 3H); 1.30–1.50 (m, 2H); 1.60–1.80 (m, 2H); 2.61 (t, 2H); 4.99 (s, 2H); 6.80–8.15 (m, 28H).

The following compounds are prepared according to the same procedure:
2-butyl-5-(2-bromophenyl)-1-[[2'-(1-triphenylmethyltetrazol-5-yl)biphenyl-4-yl]methyl]-1H-imidazole;
2-butyl-5-[3-(methoxycarbonyl)furan-2-yl]-1-[[2'-(1-triphenylmethyltetrazol-5-yl)biphenyl-4-yl]methyl]-1H-imidazole;
2-butyl-5-[3-(methoxycarbonyl)thiophen-2-yl]-1-[[2'-(1-triphenylmethyltetrazol-5-yl)thiophene-4-yl]methyl]-1H-imidazole.

EXAMPLE 7

2-Butyl-5-(2-bromophenyl)-1-[(2'cyanobiphenyl-4-yl)methyl]-1H-imidazole

A solution of 0.08 ml of triflic anhydride in 2 ml of CH$_2$Cl$_2$ under nitrogen atmosphere, cooled at −70° C., is added with a solution of 0.11 g of 4-(hydroxymethyl)-2'-cyanobiphenyl and 0.09 ml of EtNIp$_2$ in 1 ml of CH$_2$Cl$_2$. The mixture is stirred for 1h a −70° C., then 0.14 g of 1-(N-acetyl)-2-butyl-4-(2-bromophenyl)-1H-imidazole dissolved in 2 ml of CH$_2$Cl$_2$ are added. The mixture is left to warm to 25° C. and stirred for 24h. The solvent is evaporated off under reduced pressure, the residue is dissolved in 6 ml of a 2.5N NaOH:MeOH mixture (1:1) and stirred for 12h at 50° C. The solvent is removed again under reduced pressure and the residue is partitioned between water and AcOEt. The organic phase is separated, washed with a NaCl saturated solution, dried over Na$_2$SO$_4$ and the solvent is evaporated off under reduced pressure. The crude product is purified by means of flash chromatography (eluent: CH$_2$Cl$_2$:MeOH 98:2) to obtain 0.10 g of a thick oil.

$^1$H NMR (CDCl$_3$) δ: 0.90 (t, 3H); 1.31 (m, 2H) 1.72 (m, 2H); 2.66 (t, 2H); 5.03 (s, 2H); 6.91–7.90 (m, 13H).

The following compounds are prepared according to the same procedure:
2-butyl-5-[3-(methoxycarbonyl)furan-2-yl]-1-[(2'-cyanobiphenyl-4-yl)methyl]-1H-imidazole;
2-butyl-5-[3-(methoxycarbonyl)thiophen-2-yl]-1-[(2'-cyanobiphenyl-4-yl)methyl]-1H-imidazole.

EXAMPLE 8

2-Butyl-4-(2-carboxyphenyl)-1-[[2'-(1-triphenylmethyltetrazol-5-yl)biphenyl-4-yl]methyl]-1H-imidazole. (lithium salt)

0.95 g of 2-butyl-4-(2-bromophenyl)-1-[[2'-(1-triphenyl methyltetrazol-5-yl)biphenyl-4-yl]methyl]-1H-imidazole dissolved in 25 ml of anhydrous THF under nitrogen atmosphere and cooled to −70° C., are added with 0.85 ml of a solution of 1.6M BuLi in hexane. The solution is stirred for 0.5h at −70° C., thereafter CO$_2$ is bubbled therein for 20 min. The mixture is left to warm to room temperature and stirred for further 3h. The solvent is evaporated off under reduced pressure and the solid residue is suspended in 25 ml of ethyl ether and stirred for 1h, then filtered and dried, to obtain 0.45 g of an ivory powder (Yield: 50%).

$^1$H NMR (DMSO-d$_6$).

δ: 0.79 (t, 3H); 1.20 (m, 2H); 1.50 (m, 2H); 2.50 (m, 2H); 5.05 (s, 2H); 6.84–7.82 (m, 28H).

The following compounds are prepared according to the same procedure:
2-butyl-4-(3-carboxyphenyl)-1-[[2'-(1-triphenylmethyltetrazol-5-yl)biphenyl-4-yl]methyl]-1H-imidazole;
2-butyl-4-(4-carboxyphenyl)-1-[[2'-(1-triphenylmethyltetrazol-5-yl)biphenyl-4-yl]methyl]-1H-imidazole;
2-butyl-5-(2-carboxyphenyl)-1-[[2'-(1-triphenylmethyltetrazol-5-yl)biphenyl-4-yl]methyl]-1H-imidazole.

EXAMPLE 9

2-Butyl-4-(pyridin-3-yl-N-oxide)-1-[[2'-(1-triphenylmethyltetrazol-5-yl)biphenyl-4-yl]methyl]-1H-imidazole A solution of 0.65 g of 2-butyl-4-(pyridin-3-yl)-1-[[2'-(1-triphenylmethyltetrazol-5-yl)biphenyl-4-yl]methyl]-1H-imidazole in 16 ml of CHCl$_3$, at a temperature of 4° C., is added with 0 27 g of m-chloroperbenzoic acid dissolved in 10 ml of CHCl$_3$. When the addition is over, the mixture is left to warm to room temperature and stirred for 8 h, then it is washed more times with a NaHCO$_3$ saturated solution, then with a NaCl saturated solution, dried over Na$_2$SO$_4$ and the solvent is evaporated off under reduced pressure. The crude product is purified by means of flash chromatography (eluent: CH$_2$Cl$_2$:MeOH 90:10) to obtain 0.42 g of a spongy white solid (Yield: 65%).

$^1$H NMR (CDCl$_3$)

δ: 0.91 (t, 3H); 1.40 (m, 2H); 1.70 (m, 2H); 2.65 (t, 2H); 4.94 (s, 2H); 6.92–8.53 (m, 28H).

The following compounds are prepared according to the same procedure:
2-butyl-4-(pyridin-2-yl-N-oxide)-1-[[2'-(1-triphenylmethyltetrazol-5-yl)biphenyl-4-yl]methyl]-1H-imidazole (a);
2-butyl-4-(pyridin-4-yl-N-oxide)-1-[[2'-(1-triphenylmethyltetrazol-5-yl)biphenyl-4-yl]methyl]-1H-imidazole;
2-butyl-4-(4-methylpyridin-2-yl-N-oxide)-1-[[2'-(1-triphenylmethyltetrazol-5-yl)biphenyl-4-yl]methyl]-1H-imidazole;
2-butyl-4-(6-methylpyridin-2-yl-N-oxide)-1-[[2'-(1-triphenylmethyltetrazol-5-yl)biphenyl-4-yl]methyl]-1H-imidazole (b);
2-butyl-4-(4,6-dimethylpyridin-2-yl-N-oxide)-1-[[2'-(1-triphenylmethyltetrazol-5-yl)biphenyl-4-yl]methyl]-1H-imidazole;

(a) $^1$H NMR (CDCl$_3$) δ: 0.89 (t, 3H); 1.45 (m, 2H); 1.70 (m, 2H); 2.60 (t, 2H); 4.99 (s, 2H); 6.85–7.49 (m, 24H); 7.93 (m, 1H); 8.25 (d, 1H); 8.37 (dd, 1H); 8.54 (s, 1H).

(b) 1H NMR (CDCl$_3$).

δ: 0.89 (t, 3H); 1.35 (m, 2H); 1.70 (m, 2H); 2.57 (s, 3H); 2.60 (t, 2H); 4.97 (s, 2H); 6.72–7.50 (m, 24H); 7.95 (m, 1H) 8.29 (dd, 1H); 8.56 (s, 1H).

EXAMPLE 10

2-Butyl-4-(2-carboxyphenyl)-1-[[2'-(tetrazol-5-yl) -biphenyl-4-yl]methyl]-1H-imidazole 0.45 g of 2-butyl-4-(2-carboxyphenyl)-1-[[2'-(1-triphenyl methyltetrazol-5-yl)biphenyl-4-yl]methyl]-1H-imidazole are dissolved in 10 ml of THF, cooled to 0°–5° C., treated with 5 ml of 6N HCl and kept under stirring for 12h at room temperature. The mixture is cooled again and added with 10% NaOH to alkaline pH and the solvent is evaporated off under reduced pressure. The residue is taken up into 5 ml of MeOH, filtering the precipitated inorganic salts; the clear solution is evaporated to dryness and the residue is treated with 15 ml of water, filtering off the insoluble solid. Finally the solution is cooled to 0°–5° C. and acidified with 6N HCl to pH 4–5; a beige solid precipitates which is filtered, washed with water and dried. After drying, the solid is suspended in 10 ml of Et$_2$O and stirred for 1h. 0.2 g of an ivory powder are obtained (Yield: 60%).

M.p.: 135°–140° C. (dec.)

$^1$H NMR (DMSO-d$_6$).

δ: 0.86 (t, 3H); 1.31 (m, 2H); 1.59 (m, 2H); 2.58 (t, 2H); 5.22 (s, 2H); 7.07–7.18 (m, 5H); 7.48–7.84 (m, 7H); 8.45 (d, 1H).

The following compounds are prepared according to the same procedure:

2-butyl-4-(3-carboxyphenyl)-1-[[2'-(tetrazol-5-yl)biphenyl-4-yl]methyl]-1H-imidazole;
2-butyl-4-(4-carboxyphenyl)-1-[[2'-(tetrazol-5-yl)biphenyl-4-yl]methyl]-1H-imidazole;
2-butyl-4-(pyridin-2-yl)-1-[[2'-(tetrazol-5-yl)biphenyl-4-yl]methyl]-1H-imidazole (a);
2-butyl-4-(pyridin-3-yl)-1-[[2'-(tetrazol-5-yl)biphenyl-4-yl]methyl]-1H-imidazole (b);
2-butyl-4-(pyridin-4-yl)-1-[[2'-(tetrazol-5-yl)biphenyl-4-yl]methyl]-1H-imidazole;
2-butyl-4-(4-methylpyridin-2-yl)-1-[[2'-(tetrazol-5-yl)biphenyl-4-yl]methyl]-1H-imidazole;
2-butyl-4-(6-methylpyridin-2-yl)-1-[[2'-(tetrazol-5-yl)biphenyl-4-yl]methyl]-1H-imidazole (c);
2-butyl-4-(4,6-dimethylpyridin-2-yl)-1-[[2'-(tetrazol-5-yl)biphenyl-4-yl]methyl]-1H-imidazole hydrochloride (d);
2-butyl-4-(pyridin-2-yl-N-oxide)-1-[[2'-(tetrazol-5-yl)biphenyl-4-yl]methyl]-1H-imidazole (e);
2-butyl-4-(pyridin-3-yl-N-oxide)-1-[[2'-(tetrazol-5-yl)biphenyl-4-yl]methyl]-1H-imidazole (f);
2-butyl-4-(pyridin-4-yl-N-oxide)-1-[[2'-(tetrazol-5-yl)biphenyl-4-yl]methyl]-1H-imidazole;
2-butyl-4-(4-methylpyridin-2-yl-N-oxide)-1-[[2'-(tetrazol-5-yl)biphenyl-4-yl]methyl]-1H-imidazole;
2-butyl-4-(6-methylpyridin-2-yl-N-oxide)-1-[[2'-(tetrazol-5-yl)biphenyl-4-yl]methyl]-1H-imidazole hydrochloride (g);
2-butyl-4-(4,6-dimethylpyridin-2-yl-N-oxide)-1-[[2'-(tetrazol-5-yl)biphenyl-4-yl]methyl]-1H-imidazole;
2-butyl-4-(3-carboxyfuran-2-yl)-1-[[2'-(tetrazol-5-yl)biphenyl-4-yl]methyl]-1H-imidazole;
2-butyl-4-(3-carboxythiophen-2-yl)-1-[[2'-(tetrazol-5-yl)biphenyl-4-yl]methyl]-1H-imidazole (h);
2-butyl-5-(3-carboxyfuran-2-yl)-1-[[2'-(tetrazol-5-yl)biphenyl-4-yl]methyl]-1H-imidazole;
2-butyl-5-(3-carboxythiophen-2-yl)-1-[[2'-(tetrazol-5-yl)biphenyl-4-yl]methyl]-1H-imidazole;
2-butyl-5-(2-carboxyphenyl)-1-[[2'-(tetrazol-5-yl)biphenyl-4-yl]methyl]-1H-imidazole (i);
2-butyl-4-(2-carboxyphenyl)-1-[(2'-carboxybiphenyl-4-yl)methyl]-1H-imidazole;
2-butyl-4-(pyridin-2-yl)-1-[(2'-carboxybiphenyl-4-yl)methyl]-1H-imidazole (l);
2-butyl-4-(pyridin-2-yl-N-oxide)-1-[(2'-carboxybiphenyl-4-yl)methyl]-1H-imidazole;
2-butyl-4-[3-(methoxycarbonyl)thiophen-2-yl]-1-[[2'-tetrazol-5-yl)biphenyl-4-yl]methyl]-1H-imidazole (m).

(a) M.p.: 135°–140° C.
$^1$H NMR (DMSO-d$_6$) δ: 0.86 (t, 3H); 1.31 (m, 2H); 1.59 (m, 2H); 2.62 (t, 2H); 5.22 (s, 2H); 7.07–7.18 (m, 5H); 7.46–7.84 (m, 7H); 8.45 (d, 1H)

(b) M.p.: 238°–240° C.
$^1$H NMR (DMSO-d$_6$) δ: 0.85 (t, 3H); 1.32 (m, 2H); 1.57 (m, 2H); 2.73 (t, 2H); 5.29 (s, 2H); 7.09–7.25 (m, 4H); 7.42–7.75 (m, 5H); 7.92 (s, 1H); 8.15 (d, 1H); 8.46 (d, 1H); 8.97 (s, 1H)

(c) M.p.: 193°–197° C.
$^1$H NMR (DMSO-d$_6$) δ: 0.86 (t, 3H); 1.30 (m, 2H); 1.54 (m, 2H); 2.44 (s, 3H), 2.62 (t, 2H); 5.22 (s, 2H); 6.97–7.17 (m, 5H); 7.49–7.69 (m, 7H)

(d) M.P.: >250° C.
$^1$H NMR (DMSO-d$_6$) δ: 0.84 (t, 3H); 1.25 (m, 2H); 1.60 (m, 2H); 2.41 (s, 3H); 2.59 (s, 3H); 2.95 (t, 2H); 5.45 (s, 2H); 7.10–7.35 (m, 5H); 7.50–7.70 (m, 4H); 7.90 (s, 1H); 8.42 (s, 1H).

(e) M.p.: 215°–220° C. (dec.)
$^1$H NMR (DMSO-d$_6$) δ: 0.83 (t, 3H); 1.35 (m, 2H); 1.55 (m, 2H); 2.65 (m, 2H); 5.27 (s, 2H); 7.03–7.69 (m, 10H); 8.17–8.24 (m, 2H); 8.49 (s, 1H)

(f) M.p.: 245°–250° C. (dec.)
$^1$H NMR (DMSO-d$_6$) δ: 0.86 (t, 3H); 1.34 (m, 2H); 1.61 (m, 2H); 2.64 (t, 2H); 5.17 (s, 2H); 6.95–7.18 (m, 4H); 7.21–7.48 (m, 4H); 7.52 (m, 1H); 7.68 (d, 1H); 7.88 (s, 1H); 8.00 (d, 1H); 8.51 (s, 1H).

(g) M.P.: 169°–173° C. (dec.)
$^1$H NMR (DMSO-d$_6$) δ: 0.83 (t, 3H); 1.35 (m, 2H); 1.55 (m, 1H); 2.46 (s, 3H); 3.10 (t, 2H); 5.54 (s, 2H); 7.15–7.78 (m, 10H); 8.39 (dd, 1H); 8.88 (s, 1H).

(h) M.P.: >250° C.
$^1$H NMR (DMSO-d$_6$) δ: 0.86 (t, 3H); 1.30 (m, 2H); 1.55 (m, 2H); 2.67 (t, 2H); 5.29 (s, 2H); 7.14 (m, 4H); 7.39 (s, 2H); 7.50–7.75 (m, 4H); 8.00 (s, 1H).

(i) M.P.: >250° C.
$^1$H NMR (DMSO-d$_6$) δ: 0.72 (t, 3H); 1.09–1.52 (m, 4H); 2.25 (m, 2H); 5.86 (s, 2H); 7.00–7.57 (m, 13H).

(l) M.P.: 185°–189° C.
$^1$H NMR (DMSO-d$_6$) δ: 0.87 (t, 3H); 1.37 (m, 2H); 1.62 (m, 2H); 2.68 (t, 2H); 5.28 (s, 2H); 7.16–7.83 (m, 12H); 8.45 (m, 1H).

(m) M.P.: 200°–205° C. (dec.)
$^1$H NMR (DMSO-d$_6$) δ: 0.85 (t, 3H); 1.29 (m, 2H); 1.54 (m, 2H); 2.55 (t, 2H); 3.78 (s, 3H); 5.26 (s, 2H); 7.10 (s, 4H); 7.35 (s, 2H); 7.40–7.65 (m, 4H); 8.05 (s, 1H).

EXAMPLE 11

2-butyl-4(5)-[2-(methxycarbonyl)phenyl]-1H-imidazole

A solution of 0.1 g of 2-butyl-1-[2-(trimethylsilyl)ethoxymethyl]-1H-imidazole (prepared from 2-butylimidazole and [2-(trimethylsilyl)ethoxy]methyl chloride, as described by J. P. Whirten and other, J.Org.Chem. 51, 1891, (1986)) in 2 ml of a Et$_2$O:THF mixture (1:1) cooled at −70° C. and under nitrogen atmosphere, is added with 0.3 ml of 1.6M BuLi in hexane. The mixture is left under stirring for 40 min., left to warm to −30° C., then the solution is transferred through a cannula into a round-bottom flask containing 0.06 g of anhydrous ZnCl$_2$ dissolved in 3 ml of a THF:Et$_2$O mixture (1:2) at room temperature. The mixture is stirred for 2h and the resulting solution is dropped into a round-bottom flask containing 0.08 g of methyl 2-iodobenzoate and 0.01 g of NiCl$_2$(PPh$_3$)$_2$ dissolved in 3 ml of THF. The mixture is stirred for 24h at 25° C., thereafter 4 ml of 1N NH$_4$Cl cooled at 0° C. are added, the phases are separated and the aqueous phase is extracted again with Et$_2$O. The combined organic phases are washed with a NaCl saturated solution, dried over Na$_2$SO$_4$ and concentrated under vacuum. The residue is dissolved in THF and treated with the stoichiometric amount of 1N tetrabutylammonium fluoride in THF. The mixture is stirred at room temperature for 24n, then the solvent is evaporated off under reduced pressure. After purification of the crude product by means of flash chromatography (eluent: CH$_2$CH$_2$:MeOH 95:5), 0.03 g of a thick oil are obtained.

$^1$H-NMR (CDCl$_3$) δ: 0.93 (t, 3H); 1.39 (m, 2H); 1.74 (m,2H); 2.77 (t, 2H); 3.87 (s, 3H); 7.19 (s, 1H); 7.25–7.62 (m, 2H); 7.67 (d, 1H); 7.78 (d, 1H).

The following compounds are prepared according to the same procedure:
2-butyl-4(5)-[3-(methoxycarbonyl)phenyl]-1H-imidazole;
2-butyl-4(5)-[4-(methoxycarbonyl)phenyl]-1H-imidazole;
2-butyl-4(5)-[3-(methoxycarbonyl)furan-2-yl]-1H-imidazole;
2-butyl-4(5)-[3-(methoxycarbonyl)thiophen-2-yl]-1H-imidazole.

EXAMPLE 12

2-Butyl-4(5)-[3-(methoxycarbonyl)thiophen-2-yl]-1H-imidazole

A solution of 1.8 g of methyl-2-iodo-3-thiophencarboxylate and 3.8 g of 2-butyl-1-[2-(trimethylsilyl)ethoxymethyl]-5-tributylstannyl-1H-imidazole (prepared as described by R. M. Keenan et al., J. Med. Chem., 1992, 35, 3858) in 30 ml of dry toluene and under nitrogen atmosphere, is added with 0.4 g of tetrakis (triphenylphosphine) palladium[(0)]. The mixture is refluxed under stirring for 24h, then it is cooled to room temperature diluted with 50 ml of $Et_2O$ and 50 ml of a NaF saturated solution is added. The mixture is stirred for 6h and the resulting suspension is filtered on a celite pad. The organic phase is separated and washed with brine, dried over $Na_2SO_4$ and concentrated under vacuum. The residue is dissolved in THF and treated with the stoichiometric amount of 1N tetrabutylammonium fluoride in THF. The mixture is stirred at room temperature for 24h, then the solvent is evaporated off under reduced pressure.

After purification of the crude product by means of flash chromatography (eluent: hexane:AcOEt 50:50), 0.5 g of a low-melting solid is obtained.

$^1$H NMR ($CDCl_3$) δ: 0.95 (t, 3H); 1.50 (m, 2H); 1.80 (m, 2H); 2.79 (t, 2H); 3.90 (s, 3H); 7.01 (d, 1H); 7.38 (d, 2H).

The following compounds are prepared according to the same procedure:
2-butyl-4-(5)-(pyridin-2-yl)-1H-imidazole (a);
2-butyl-4-(5)-(6-methylpyridin-2-yl)-1H-imidazole (b).

(a) $^1$H NMR ($CDCl_3$)
δ: 0.85 (t, 3H); 1.35 (m, 2H); 1.68 (m, 2H); 2.75 (t, 2H); 7.11 (m, 1H); 7.45 (s, 1H); 7.67 (m, 2H); 8.42 (m, 1H).

(b) $^1$H NMR ($CDCl_3$)
δ: 0.90 (t, 3H); 1.40 (m, 2H); 1.73 (m, 2H); 2.50 (s, 3H); 2.75 (t, 2H); 6.95 (d, 1H); 7.47 (s, 1H); 7.48–7.62 (m, 2H).

EXAMPLE 13

2-Butyl-4-[6-hydroxypyridin-2-yl]-1-[[2'-(1H-tetrazol-5-yl)biphenyl-4-yl]methyl]-1H-imidazole A solution of 0.35 g of 2-butyl-4-(pyridin-2-yl-N-oxide)-1-[[2'-(1-triphenylmethyl-tetrazol-5-yl)biphenyl-4-yl]methyl]-1H-imidazole in 7 ml of acetic anhydride is refluxed for 3 h, then the solvent is evaporated off under reduced pressure and the remaining oil is dissolved in 3 ml of THF and 2 ml of 6N HCl. The mixture is stirred for 12 h at room temperature, then the solvent is evaporated off under vacuum. After purification of the crude product by means of flash chromatography (eluent: $CH_2Cl_2$:MeOH:AcOH 88:10:1), 0.13 g of a yellow solid is obtained (yield: 55%).
M.P.: 220°–225° C. (dec.)

$^1$H NMR (DMSO-$d_6$) δ: 0.85 (t, 3H); 1.35 (m, 2H); 1.61 (m, 2H); 3.05 (m, 2H); 5.56 (s, 2H); 7.32–7.59 (m, 9H); 8.51 (m, 2H); 8.84 (s, 1H).

We claim:

1. Compounds of general formula (I):

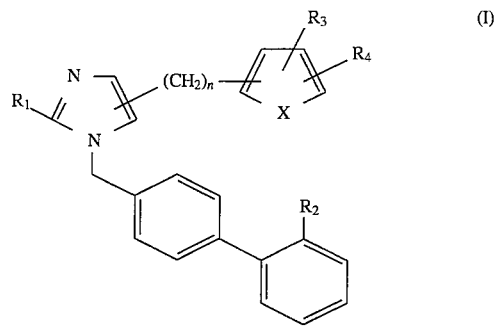

wherein:

n is 0, 1 or 2

X is O, S,

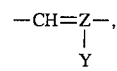

wherein Z is C or N, whereas Y is H, when Z is C or oxygen or it is not present, when Z is the same as N;

$R_1$ is $C_1$–$C_5$ straight, branched or cyclic alkyl, or a $C_2$–$C_5$ alkenyl group;

$R_2$ is a —$COOR_5$ group, —CN, a $SO_3H$ group, or a tetrazole group of general formula (IIa) or (IIb):

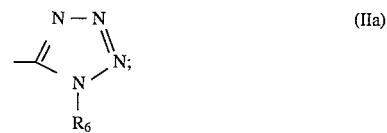

$R_3$, $R_4$ are independently H, halogen, CN, $NO_2$, $NH_2$, $COR_7$, $OR_8$, $CH_2OR_8$, $C_1$–$C_5$ straight or branched alkyl;

$R_5$ is H, $C_1$–$C_5$ straight or branched alkyl, benzyl;

$R_6$ is H, $C_1$–$C_5$ alkyl, triphenylmethyl;

$R_7$ is H, $OR_8$, $NR_9R_{10}$;

$R_8$ is H, $C_1$–$C_5$ straight or branched alkyl, benzyl;

$R_9$, $R_{10}$ are independently H, $C_1$–$C_5$ alkyl;

and the salts thereof with pharmaceutically acceptable acids and bases.

2. Compounds according to claim 1, wherein the aryl or heteroaryl group of general formula:

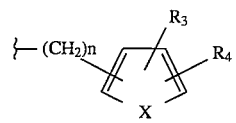

is linked at the 4-position of the imidazole ring and wherein n, X, $R_3$, $R_4$ have the meanings defined above.

3. Compounds according to claim 1, wherein the aryl or heteroaryl group of general formula

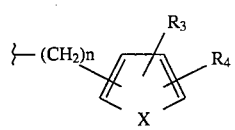

is linked at the 5-position of the imidazole ring and wherein n, X, $R_3$, $R_4$ have the meanings defined above.

4. Compounds according to claim 3, wherein $R_1$ is selected from propyl and butyl, X is —CH=CH—, and $R_3$ is a —COOH group.

5. Compounds according to claim 4, which are:
2-butyl-4-(2-carboxyphenyl)-1-[[2'-(1H-tetrazol-5-yl)-biphenyl-4-yl]methyl]-1H-imidazole;
2-butyl-4 -(3-carboxyphenyl)-1-[[2'-(1H-tetrazol-5-yl)-biphenyl-4-yl]methyl]-1H-imidazole;
2-butyl-4-(4-carboxyphenyl)-1-[[2'-(1H-tetrazol-5-yl)-biphenyl-4-yl]methyl]-1H-imidazole;
2-butyl-5-(2-carboxyphenyl)-1-[[2'-(1H-tetrazol-5-yl)-biphenyl-4-yl]methyl]-1H-imidazole; and
2-butyl-4-(2-carboxyphenyl)-1-[(2'-carboxybiphenyl-4-yl)methyl]-1H-imidazole.

6. Compounds according to claim 3, wherein $R_1$ is selected from: propyl, or butyl, X is O, S, —C=N—, or

and $R_3$ is selected from H, methyl, ethyl, propyl, COOH, or —COOH$_3$.

7. Compounds according to claim 6, which are:
2-butyl-4-(pyridin-2-yl)-1-[[2'-(1H-tetrazol-5-yl)biphenyl-4-yl]methyl]-1H-imidazole;
2-butyl-5-(3-carboxythiophen-2-yl)-1-[[2'-(1H-tetrazol-5-yl)biphenyl-4-yl]methyl]-1H-imidazole;
2-butyl-5-(3-carboxyfuran-2-yl)-1-[[2'-(1H-tetrazol-5-yl)biphenyl-4-yl]methyl]-1H-imidazole;
2-butyl-4-(pyridin-3-yl)-1-[[2'-(1H-tetrazol-5-yl)biphenyl-4-yl]methyl]-1H-imidazole;
2-butyl-4-(pyridin-4-yl)-1-[[2'-(1H-tetrazol-5-yl)biphenyl-4-yl]methyl]-1H-imidazole;
2-butyl-4-(4-methylpyridin-2-yl)-1-[[2'-(1H-tetrazol-5-yl)biphenyl-4-yl]methyl]-1H-imidazole;
2-butyl-4-(6-methylpyridin-2-yl)-1-[[2'-(1H-tetrazol-5-yl)biphenyl-4-yl]methyl]-1H-imidazole;
2-butyl-4-(4,6-dimethylpyridin-2-yl)-1-[[2'-(1H-tetrazol-5-yl )biphenyl-4-yl]methyl]-1H-imidazole;
2-butyl-4-(pyridin-2-yl-N-oxide)-1-[[2'-(1H-tetrazol-5-yl)biphenyl-4-yl]methyl]-1H-imidazole;
2-butyl-4-(pyridin-3-yl-N-oxide)-1-[[2'-(1H-tetrazol-5-yl)biphenyl-4-yl]methyl]-1H-imidazole;
2-butyl-4-(pyridin-4-yl-N-oxide)-1-[[2 '-(1H-tetrazol-5-yl)biphenyl-4-yl]methyl]-1H-imidazole;
2-butyl-4-(4-methylpyridin-2-yl-N-oxide)-1-[[2 '-(2H-tetrazol-5-yl)biphenyl-4-yl]methyl]-1H-imidazole;
2-butyl-4-(6-methylpyridin-2-yl-N-oxide)-1-[[2'-(1H-tetrazol-5-yl)biphenyl-4-yl]methyl]-1H-imidazole;
2-butyl-4-(4,6-dimethylpyridin-2-yl-N-oxide)-1-[[2'-(1H-tetrazol-5-yl)biphenyl-4-yl]methyl]-1H-imidazole;
2-butyl-4-(3-carboxyfuran-2-yl)-1-[[2'-(1H-tetrazol-5-yl)biphenyl-4-yl]methyl]-1H-imidazole;
2-butyl-4-(3-carboxythiophen-2-yl)-1-[[2'-(1H-tetrazol-5-yl)biphenyl-4-yl]methyl]-1H-imidazole;
2-butyl-4-(pyridin-2-yl)-1-[(2'-carboxybiphenyl-4-yl)methyl]-1H-imidazole; and
2-butyl-4-(pyridin-2-yl-N-oxide)-1-[(2'-carboxybiphenyl-4-yl)methyl]-1H-imidazole.

8. A process for the preparation of the compounds of claim 1, which process comprises reacting a compound of general formula (III):

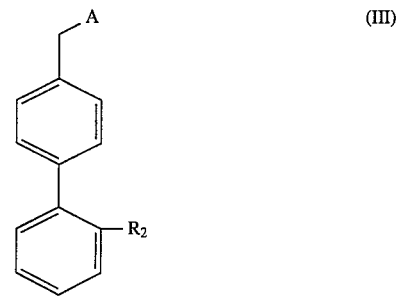

wherein A is Cl, Br, I, OCOCH$_3$, OSO$_2$CH$_3$, OSO$_2$CF$_3$ and $R_2$ is a COOR$_5$ group, wherein $R_5$ is C$_1$–C$_5$ straight or branched alkyl or benzyl, a CN group, a tetrazole group of general formula (IIa) or (IIb), wherein $R_6$ is a triphenylmethyl or C$_1$–C$_5$ alkyl group, with a compound of general formula (IV):

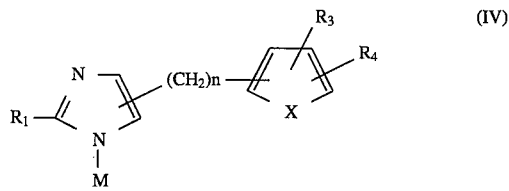

wherein M is H, —COCH$_3$, p-methoxybenzyl and X, n, $R_1$, $R_3$, $R_4$ have the meanings defined above.

9. A process for the preparation of the compounds of claim 1, which process comprises reacting a compound of general formula (VIII):

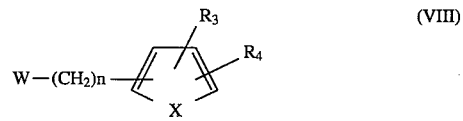

wherein W is Br, I or ZnCl, Bu$_3$Sn, Me$_3$Sn, B(OH)$_2$ and n, X, $R_3$, $R_4$ have the meanings reported above, with a compound of general formula (VII):

wherein $R_1$ has the meaning reported above, P is a —CH$_2$N(CH$_3$)$_2$ or —CH$_2$OCH$_2$CH$_2$Si(CH$_3$)$_3$ protecting group and Q is ZnCl, Me$_3$Sn, Bu$_3$Sn, B(OH)$_2$ or Br or I, in the presence of a complex of a transition metal as the catalyst, and subsequently reacting it with a compound of general formula (III)

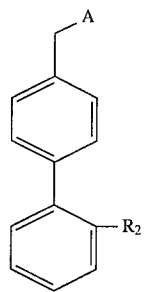 (III)

wherein A is Cl, Br, I, OH, OCOCH$_3$, OSO$_2$CH$_3$, OSO$_2$CF$_3$ and R$_2$ is a COOR$_5$ group, wherein R$_5$ is C$_1$–C$_5$ straight or branched alkyl or benzyl, a CN group, a tetrazole group of general formula (IIa) or (IIb), wherein R$_6$ is a triphenylmethyl or C$_1$–C$_5$ alkyl group.

10. Pharmaceutical compositions containing as the active principle an effective amount of one or more compounds according to claims 1–7, in combination with suitable excipients.

11. A method for treating a patient suffering from a cardiac, vascular or renal disorder which comprises administering to said patient an effective amount of a composition according to claim 10.

* * * * *